United States Patent [19]

Vora

[11] 4,447,653

[45] May 8, 1984

[54] ADSORBENT REGENERATION IN INTEGRATED ETHERIFICATION PROCESS

[75] Inventor: Bipin V. Vora, Elk Grove Village, Ill.

[73] Assignee: UOP Inc., Des Plaines, Ill.

[21] Appl. No.: 395,413

[22] Filed: Jul. 6, 1982

[51] Int. Cl.³ .................... C07C 41/06; C07C 41/00
[52] U.S. Cl. .................................. 568/697; 568/699; 568/917
[58] Field of Search ................................ 568/697, 699

[56] References Cited

U.S. PATENT DOCUMENTS

| | | | |
|---|---|---|---|
| 2,720,547 | 10/1955 | Wolff et al. | 260/614 |
| 2,943,105 | 6/1960 | Caruthers | 260/450 |
| 3,489,808 | 1/1970 | Eberly, Jr. | 260/674 |
| 3,726,942 | 4/1973 | Louder | 260/683.61 |
| 3,931,350 | 1/1976 | Sparks | 260/671 B |
| 4,098,684 | 7/1978 | Innes | 208/245 |
| 4,118,425 | 10/1978 | Herbstman | 260/614 A |
| 4,219,678 | 8/1980 | Obenaus et al. | 568/697 |
| 4,252,541 | 2/1981 | Herbstman | 44/56 |
| 4,322,565 | 3/1982 | Dotson et al. | 568/697 |
| 4,329,516 | 5/1982 | Muddarris | 568/697 |
| 4,371,718 | 2/1983 | Hutson | 568/697 |

FOREIGN PATENT DOCUMENTS 2050379A 1/1981 United Kingdom .

OTHER PUBLICATIONS

Chemical & Engineering News, Jun. 25, 1979, pp. 35–36, "New Plants, Processes Set for Octane Booster" by Stephen C. Stinson.

Paper presented at AIChE Meeting, Philadelphia, Jun. 4–8, 1978, pp. 271–275, "Huls-Process: Methyl Tertiary Butylether" by Fritz Obenaus and W. Droste.

Oil & Gas Journal, Nov. 10, 1980, pp. 191–197, "Catalytic LPG Dehydrogenation Fits in '80's Outlook" by Roy C. Berg et al.

*Primary Examiner*—Howard T. Mars
*Attorney, Agent, or Firm*—James R. Hoatson, Jr.; John F. Spears, Jr.; William H. Page, II

[57] ABSTRACT

An improved method is disclosed for regenerating adsorbents used in an integrated process for the production of ethers such as methyl tertiary butyl ether by the reaction of an alcohol with an isoolefin. The sorbents are used to remove such compounds as the product ether and the feed alcohol from a hydrocarbon recycle stream withdrawn from the etherification zone. The regeneration procedure includes contacting the sorbent with a portion of the treated hydrocarbon stream. The resultant contaminated hydrocarbon stream is passed into a stripping column used to remove light ends from the effluent of a dehydrogenation zone in which the isoolefin fed to the etherification zone is produced. The hydrocarbonaceous compounds collected on the sorbent are thus recycled rather than being destroyed or lost in low purity effluent streams. The contaminated hydrocarbon stream may also be passed directly into the etherification zone.

5 Claims, 1 Drawing Figure

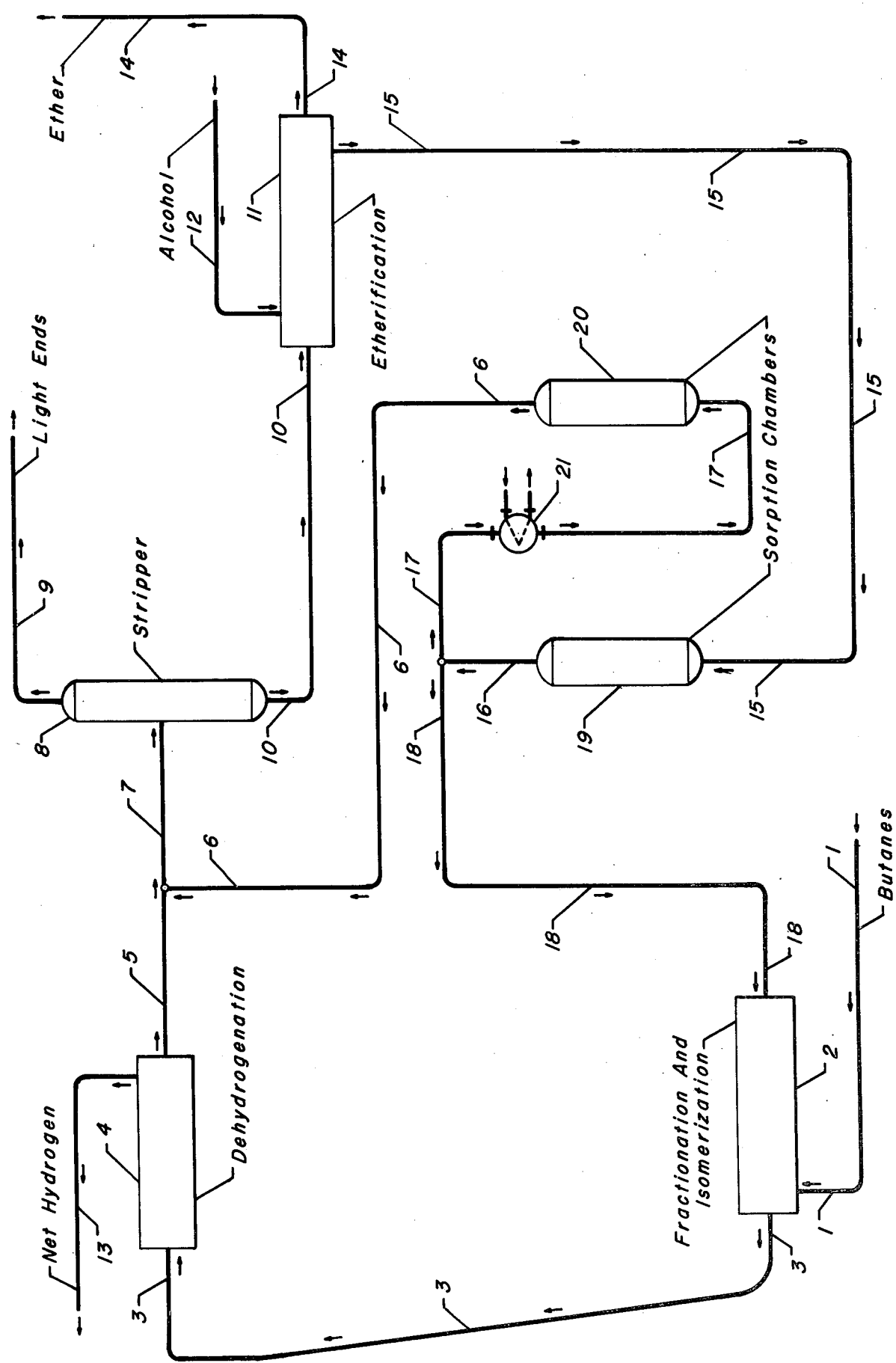

ADSORBENT REGENERATION IN INTEGRATED ETHERIFICATION PROCESS

FIELD OF THE INVENTION

The invention relates to an integrated process for the production of ethers by the reaction of an alcohol with an isoolefin. The invention more directly relates to such an integrated process wherein methyl tertiary butyl ether is produced by the reaction of methanol and isobutylene. The invention specifically relates to the regeneration of solid sorbents used to selectively remove oxygen-containing compounds and possibly other undesired compounds from a C4 hydrocarbon recycle stream of such an integrated process.

PRIOR ART

The production of ethers by the reaction of an isoolefin with an alcohol is well known and is practiced commercially. This highly selective reaction is also used to remove isoolefins, especially isobutylene, from mixed hydrocarbon streams such as the C4 streams produced in an ethylene producing steam cracking plant or in an FCC unit. Increased attention has been recently focused on ether production due to the rapidly increasing demand for lead-free octane boosters for gasoline such as methyl tertiary butyl ether (MTBE).

A detailed description of processes, including catalysts, processing conditions and product recovery, for the production of MTBE from isobutylene and methanol are provided in U.S. Pat. Nos. 2,720,547 and 4,219,678 and in an article at page 35 of the June 25, 1979 edition of *Chemical and Engineering News*. The preferred etherification zone is described in a paper presented at the American Institute of Chemical Engineers 85th National meeting on June 4-8, 1978 by F. Obenaus et al.

Descriptions of integrated processes for producing MTBE, including those which utilize butane isomerization and/or butane dehydrogenation, are found in U.S. Pat. Nos. 3,726,942; 4,118,425 and 4,252,541 and in U.K. patent application No. 2,050,379A (priority date May 28, 1979). The last of these references is believed the most pertinent to this application because of the arrangement of the process steps and the similar operation of the various process steps. FIG. 6 of an article at page 191 of the Nov. 10, 1980 edition of *The Oil and Gas Journal* is also pertinent since it presents an integrated process for producing MTBE from mixed butanes having a flow similar to that shown in the subject Drawing. The flow paths of most process streams are the same in this reference and in the preferred embodiment of the subject process with the exceptions that a normal butylene hydrogenation zone is shown in place of the adsorption zone used the subject process. In addition no regeneration streams are shown in this reference.

It is also well known to use a solid adsorbent, such as alumina or zeolitic materials, to treat liquid phase hydrocarbon process streams for the removal of small quantities of undesired contaminants. These adsorbents have been used to remove water, sulfur compounds and various hydrocarbonaceous compounds including such oxygenated compounds as alcohols from process streams. This use of adsorbents is taught in U.S. Pat. Nos. 2,943,105; 3,489,808; 3,931,350 and 4,098,684. Previously cited U.S. Pat. No. 3,726,942 discloses removing methanol from the unreacted hydrocarbons withdrawn from an MTBE reaction zone through the use of molecular sieves.

BRIEF SUMMARY OF THE INVENTION

The invention provides a method of regenerating solid sorbents used in an integrated etherification process to remove oxygenates from a recycle stream. The method comprises contacting the used sorbent with a high temperature stream comprising a hydrocarbon present in the process and then passing the regenerent stream directly into the etherification zone or more preferably into a dehydrogenation unit stripping column located upstream of the etherification unit. The feed alcohol and product ether of the process present in the regenerent stream are preferably concentrated into the bottoms stream of the stripping column, which is passed into the etherification zone. These valuable compounds are thereby recycled for eventual recovery in a closed loop system.

The invention may be characterized as a process for the production of an ether which comprises the steps of passing a first process stream comprising an isoparaffin through a dehydrogenation zone and thereby producing a reaction zone effluent stream comprising the isoparaffin and a corresponding isoolefin; passing the reaction zone effluent stream and a second process stream into a stripping column and producing a stripping column bottoms stream comprising the isoparaffin, the isoolefin and oxygenates and which is substantially free of ethane; passing the stripping column bottoms stream and an alcohol feed stream into an etherification zone, and withdrawing from the etherification zone a product stream comprising the ether and a hydrocarbon recycle stream comprising the isoparaffin and oxygenates; removing oxygenates from the hydrocarbon recycle stream by contacting the recycle stream with a selective sorbent in a sorption zone; processing the recycle stream to effect the production of additional amounts of the isoolefin; regenerating exhausted sorbent in the sorption zone by a procedure which comprises contacting at least a portion of the sorbent with a heated regeneration stream comprising the isoparaffin and thereby producing a regenerent stream comprising the isoparaffin and the oxygenates which is passed into the stripping column as the previously referred to second process stream.

BRIEF DESCRIPTION OF THE DRAWING

The Drawing illustrates the overall flow of an integrated process for producing ethers in which the preferred embodiment of the inventive concept is employed in the regeneration of the sorbent used to treat the hydrocarbon recycle stream flowing through lines 15 and 18. A butane feed stream comprising isobutane and normal butane enters a fractionation and butane isomerization zone 2 through line 1. The isobutane of this stream and the recycle stream together with the isobutane produced by the isomerization of normal butane from this stream and the recycle stream is concentrated into an isobutane stream passed into the dehydrogenation zone 4 via line 3. The isobutane stream is therein contacted with a dehydrogenation catalyst at dehydrogenation conditions to produce hydrogen removed through line 13 and a dehydrogenation reactor effluent comprising isobutane and isobutylene carried by line 5.

The dehydrogenation reactor effluent stream is combined with a regenerent stream carried by line 6 and passed into a stripping column 8 via line 7. The light ends present in the admixture of these two streams, such as ethane and dimethyl ether, are removed from the process in line 9 as the net overhead stream of the stripping column. The net bottoms stream of the stripping column, which contains C$_4$ hydrocarbons and the less volatile oxygenates present in the regenerent stream, is passed into the etherification zone 11 through line 10. The isobutylene fed to this zone reacts with the alcohol, preferably methanol, charged to the process through line 12 to produce an ether which is withdrawn from the process as the product stream of line 14.

A hydrocarbon recycle stream is withdrawn from the etherification zone via line 15 and passed through the adsorption chamber 19 of a multichamber adsorption zone. The adsorbent selectively removes small amounts of the product ether, the feed alcohol and other oxygenates from the recycle stream. The major portion of the recycle stream is then preferably passed into the fractionation section of the fractionation and isomerization zone via lines 16 and 18. This recycle stream is predominantly isobutane but normally also contains normal butane. A small portion of the recycle stream is diverted through line 17 and heated by indirect heat exchange in heater 21. This portion of the recycle stream is then passed through a second adsorption chamber 20 as part of the regeneration procedure for the adsorbent present within this chamber. This regenerent stream removes oxygenates from the adsorbent, and the regenerent stream then carries the oxygenates into column 8 via lines 6 and 7. The use and regeneration of the chambers is periodically alternated to provide continuous operation.

DETAILED DESCRIPTION

Etherification processes have been constructed and proposed for the production of various ethers as either end products or as intermediates in process for producing other valuable chemical compounds. For instance, plans have been announced to produce pure isobutane for the manufacture of polyisobutylenes and tert-butylphenol by first producing MTBE and then cracking the MTBE to yield isobutylene and methanol which is recycled. Large amounts of MTBE are also being produced for use as anti-knock compounds in lead-free gasoline. Etherification processes therefore find utility in both the petrochemical and petroleum refining industries.

The majority of the description of the invention is presented in terms of the reaction of isobutylene with methanol to form MTBE since these are the preferred feed materials and the commercially predominant reaction. However, it is not intended to thereby lessen the scope of the inventive concept, which may be applied in the production of other ethers when a similar hydrocarbon recycle stream and stripping column are present in the process. The inventive concept may therefore be applied in general to the reaction of isoolefins having less than six carbon atoms per molecule with water-soluble alcohols which preferably have less than four carbon atoms per molecule. The next preferred alcohol after methanol is ethanol but other alcohols such as propanols, ethylene glycol or propylene glycol can also be consumed in the process. The isoolefin is preferably derived by dehydrogenation of isobutane or isopentane. The subject process may therefore be employed in the production of a wide variety of ethers other than MTBE including methyl tertiary amyl ether, ethyl tertiary amyl ether and ethyl tertiary butyl ether.

The ethers are produced by the reaction of the alcohol and the isoolefin in an etherification zone. The ethers are then separated from unreacted hydrocarbons, water and unreacted alcohol to yield the ether product stream. In the case of MTBE production, the unreacted hydrocarbons include normal butenes, formed from normal butane which enters the dehydrogenation zone, and possibly various butadienes also formed in the dehydrogenation zone since these compounds do not react with the alcohol. Also normally present is a larger amount of isobutane remaining from the isobutane present in the dehydrogenation zone feed stream which was not dehydrogenated. These unreacted hydrocarbons are withdrawn from the separatory facilities used to recover the ether as a separate hydrocarbon stream.

In the integrated processes to which the subject invention is directed, this hydrocarbon stream is recycled to produce more of the isoolefin, normally by the sequential steps of isomerization and dehydrogenation, and is therefore referred to as the hydrocarbon recycle stream. If not removed from the process, the normal butenes and any butadienes present in the recycle stream will accumulate within the process and cause the hydrocarbon recycle stream to increase in volume. The presence of these compounds also has detrimental effects on the preferred dehydrogenation catalyst. Other components of the hydrocarbon recycle stream include smaller amounts of various oxygenates such as the product ether, the feed alcohol and oxygen-containing reaction by-products, such as dimethylether, resulting from side reactions. It is also not desirable to pass these oxygenates into the isomerization or dehydrogenation zones because of their effects on the preferred catalysts. It is therefore desirable to remove, alter or destroy all of these undesired compounds before the hydrocarbon recycle stream is passed into the isomerization and dehydrogenation zones.

Heretofore it has been the practice to remove undesired compounds from the hydrocarbon recycle stream by hydrotreating. That is the olefins, diolefins and oxygenates were hydrogenated to form paraffins. Hydrotreating the hydrocarbon recycle stream can add considerably to the capital and operating costs of the overall process. However, it has recently been found that solid sorbents may be used to remove the undesired compounds from the recycle stream and that these sorbents may be regenerated. It is an objective of the subject invention to provide an integrated etherification process employing regeneration of the recycle stream sorbent. It is a further objective of the subject invention to reduce the cost and difficulty of regenerating sorbents used to remove oxygenates from the recycle stream of integrated etherification processes. It is another objective of the subject invention to provide a method of recovering valuable oxygenated hydrocarbonaceous compounds, such as product MTBE, present in the C$_4$ hydrocarbon recycle stream of an integrated process for producing MTBE.

In the subject process oxygen-containing hydrocarbonaceous compounds, and possibly other compounds as described below, are removed from the hydrocarbon recycle stream by contacting the recycle stream with a sorbent solid. The sorbent, which may function as a physical or as a chemical adsorbent, is preferably disposed as a fixed bed in two or more cylindrical contacting chambers. The flow of the recycle stream is preferably switched between different chambers to allow continuous processing of the recycle stream while the sorbent in the chambers which are not being used is either regenerated or replaced depending on the regenerability and remaining capacity of the sorbent. The sorbent may also be contained in a different chamber configuration such as a moving bed or a fluidized bed.

The required sorption-promoting conditions will depend on such factors as the specific sorbent used in the process and the chemical compounds to be removed from the recycle stream. A general range of suitable sorption-promoting conditions includes a superatmospheric pressure less than about 500 psig, although higher pressures may be employed, and a temperature less than about 160° F. (71° C.). A liquid hourly space velocity of less than 10 hr.$^{-1}$ should be employed. A preferred range of sorption-promoting conditions includes a pressure between 10 and about 200 psig, a temperature between 50° and 150° F. (10° and 65° C.) and a liquid hourly space velocity between 0.3 and 3.0 hr$^{-1}$.

The sorbent is preferably in the form of solid spherical particles on the order of about 1/16 to ¼ of an inch in diameter. The preferred sorbents are the zeolitic materials known as molecular sieves and ion exchange resins. The selection of sorbents for use in the subject process is dependent on the effectiveness, selectivity and regenerability of the particular solid and is not dependent on the manner in which the sorbent acts to remove the undesired compounds. The sorbent may therefore act by physical or chemical adsorption or by ion exchange. As is known to those skilled in the art these materials are normally selective as to the compounds they tend to sorb, and it is therefore necessary to carefully select the proper materials. Small scale testing may be required in some instances as part of the selection process to determine the appropriateness of materials other than those listed herein. It is contemplated that the solid sorbent may also be chosen from the group consisting of natural and synthetic aluminas, clays, charcoals and other known sorbents. The preferred sorbents are type 5A and type 13X molecular sieves which should remove both the oxygen-containing impurities and some sulfur compounds which may be present in the feed stream such as dimethylsulfoxide. A type 3A molecular sieve may be employed to remove water from the recycle hydrocarbon stream. The terms "sorbent" and "adsorbent" and the terms "sorption" and "adsorption" are at times used interchangeably herein since the use of materials commonly referred to as adsorbents is highly preferred.

The regeneration of the sorbents may include a low temperature hydrogen stripping step in which the temperature of the hydrogen stream is gradually increased. The hydrogen regeneration gas stream preferably contains at least 85 mole percent hydrogen and has an initial temperature below 200° F. (93° C.). The temperature of the gas stream is gradually increased at a rate less than about 50 Fahrenheit degrees until a temperature is reached in the range of about 300°–600° F. (149°–315° C.). Heated hydrocarbons can then be employed if desired to reach higher regeneration temperatures. It is also possible that the low temperature hydrogen stripping step may not be required and that conventional regeneration procedures such as pressure reduction and/or initial high temperature hydrocarbon, steam or nitrogen purging may be employed. The preferred "swing bed" regeneration of the sorbent includes contacting a contaminated off-stream bed of the sorbent with a heated portion of the previously treated hydrocarbon recycle stream or other regenerent hydrocarbon. This stream should have a temperature above 250° F. (121° C.) and preferably above 300° F. (149° C.). Regeneration conditions also include a superatmospheric pressure preferably less than 250 psig. Another preferred source of the regenerent hydrocarbon is the stabilizer of the isomerization zone used in the process. This is especially true when a sorptive treating step requiring the use of hot regenerent is also performed in the isomerization zone. Common regenerent preparation facilities can then be employed.

The preferred regeneration media is a heated liquid phase stream. Alternatively the regeneration media may be a vapor phase stream. When a vapor stream is employed it is preferably condensed, if feasible, to recover the compounds removed from the sorbent during regeneration. It is preferred that liquid-phase regenerent be used and that the oxygenate-containing regenerent liquid is passed into the stripping column by admixture with the dehydrogenation reaction zone effluent stream. However, the regenerent may if desired be passed separately into the stripping column. The passage of the regenerent into the stripping column allows the rejection of more volatile impurities such as dimethyl ether as part of the overhead stream of the stripping column. In a less preferred embodiment of the invention, the regenerent stream is passed directly into the etherification zone as by admixture into the bottoms stream of the stripping column. It is contemplated that this embodiment would be utilized when an alcohol other than methanol and/or a different etherification process was employed. That is, this embodiment would be employed when the light oxygenates would not be removed as part of the stripper overhead stream but can be recovered from the etherification zone as, for instance, part of the etherification product stream.

The classification of chemical compounds present in the hydrocarbon recycle stream as undesired compounds or as impurities will depend on such factors as the identity of the reacting alcohol and isoolefin and the susceptibility of the downstream catalyst(s) to poisoning or deactivation by the various compounds. Some of the compounds which it is desired to remove may be derived from the hydrocarbon feed stream if the feed stream is admixed into the recycle stream upstream of the sorption zone. However, it is believed that most or all of the compounds which it is desired to remove from the hydrocarbon recycle stream will normally be present in the recycle stream as it leaves the etherification zone. These compounds include the product ether, the feed alcohol and oxygen-containing reaction by-products. In the case of MTBE production, these compounds are MTBE, methanol and by-products including dimethyl ether and tertiary butyl alcohol. Up to 90 percent of the total oxygenates will be dimethyl ether.

Since the recycle stream is normally water washed to remove the vast majority of the water-soluble alcohols such as methanol, the recycle stream will contain water and most probably will be saturated with water. This water may also be removed from the recycle stream, if desired, by the sorbent. The recycle hydrocarbon stream will also contain mono- and diolefins produced in the dehydrogenation zone. In the preferred embodiment, these olefins are isobutylene and normal butylene and butadienes. It is preferred that most of the olefinic hydrocarbons present in the recycle stream are not removed during contact with the sorbent. Therefore, preferably less than 5 mole percent of any butadiene present in the recycle stream is removed from the recycle stream by contact with the solid sorbent. The thus-treated hydrocarbon recycle stream is then passed into the deisobutanizer or other appropriate facility. If the normal butane content of the recycle hydrocarbon stream is very low, it can be passed directly into the dehydrogenation zone.

The removal of oxygen-containing compounds from the recycle stream may by itself be sufficient to eliminate any requirement for hydrotreating the recycle stream. This assumes that the olefinic components are at a level which is tolerable in the downstream portion of the overall integrated process either due to a very low concentration of the olefinic compounds in the recycle stream or the ability of the catalysts to function properly with feed streams containing such mono- and diolefins. The characteristics of the catalysts will therefore be very significant in determining the required treatment for the recycle stream since the dehydrogenation catalyst's tendency to produce diolefinic hydrocarbons largely determines the concentration of diolefins in the recycle stream.

In the preferred form of the overall integrated etherification process the net effluent stream of the dehydrogenation reaction zone, which comprises a mixture of olefins and saturated hydrocarbons, is fed to an etherification zone together with the feed alcohol. The etherification zone may take many different forms but is preferably similar to that described in U.S. Pat. No. 4,219,678 and shown in the previously cited paper. In this instance the isobutane or other isoolefin, methanol or other feed alcohol, and a recycle stream containing the product ether, and methanol are passed into the reaction zone in which they are contacted with an acidic catalyst while maintained at etherification conditions. A wide range of materials is known to be effective as etherification catalysts for the preferred reactants including mineral acids such as sulfuric acid, boron trifluoride, phosphoric acid on kieselguhr, phosphorus-modified zeolites and various sulfonated resins. The use of a sulfonated solid resin catalyst is preferred. These resin-type catalysts include the reaction products of phenol-formaldehyde resins and sulfuric acid and sulfonated polystyrene resins including those cross-linked with divinylbenzene. Further information on suitable etherification catalysts may be obtained by reference to U.S. Pat. Nos. 2,480,940; 2,922,822; and 4,270,929 and the previously cited etherification references.

A broad range of etherification conditions includes a superatmospheric pressure sufficient to maintain the reactants as a liquid phase, generally below about 200 psig, and a temperature between about 30° and about 100° C. A preferred temperature range is from 50° to 100° C. The reaction rate is normally faster at higher temperatures but conversion is more complete at lower temperatures. High conversion in a moderate volume reaction zone can therefore be obtained if the initial section of the reaction zone, e.g. the first two-thirds, is maintained above 70° C. and the remainder of the reaction zone is maintained below 50° C. This may be accomplished most easily with two reactors. The ratio of feed alcohol to isoolefin should normally be maintained in the broad range of from 1:1 to 2:1. With the preferred reactants good results are achieved if the ratio of methanol to isobutene is between 1.1:1 and 1.5:1. An excess of methanol above that required to achieve satisfactory conversion at good selectivity should be avoided.

It is preferred that the effluent of the etherification reaction zone is passed into an intermediate point of a fractionation column designed and operated to concentrate unconverted isoolefins present in the effluent into a net overhead stream. In the case of isobutene being the isoolefin, this column is a deisobutanizer. The net overhead stream of this column becomes the recycle hydrocarbon stream of the subject process and is passed into the sorption zone, preferably after passage through a water wash zone to recover most of the methanol or other alcohol present in this stream. The bottoms stream of this column contains most of the product ether and excess alcohol present in the reaction zone effluent stream and is passed into a second fractionation column. By proper operation of the second column the entering materials may be separated into a net overhead stream which is an alcohol-ether azeotrope and a bottoms stream of relatively pure product ether which is withdrawn as the product stream of the process. The alcohol-ether azeotrope is preferably recycled to the beginning of the reaction zone. Further details on the separatory method and other aspects of the etherification zone may be obtained from the previously cited references.

After the hydrocarbon recycle stream has passed through the sorption zone, the recycle stream is passed into a fractionation section of a fractionation and isomerization zone. Preferably this fractionation section comprises a single fractionation column but two or more columns could be employed if desired. This column is normally referred to as a deisobutanizer. The recycle stream should enter the column at an upper intermediate point. The isoparaffin component of the recycle stream and other streams entering the deisobutanizer becomes concentrated into the net overhead stream of the column and is passed into the dehydrogenation zone. Normal paraffins are removed from the column as part of a lower sidecut stream which is preferably passed into an optional paraffin isomerization unit. The overhead stream of the column should be rich in the isoparaffin and the sidecut stream should be rich in the normal paraffin. As used herein the term "rich" is intended to indicate that the process stream contains at least 55 mole percent of the particular chemical compound or class of compounds which is specified.

The isobutane-rich overhead stream of the deisobutanizer is passed into a butane dehydrogenation reaction zone. This zone will contain a reaction zone and associated auxiliary process equipment such as condensers and a vapor-liquid separator which receives the partially condensed reactor effluent stream. A hydrogen-rich gas stream is preferably separated from the liquid condensed from the reactor effluent. A portion of this gas will normally be recycled and the remainder will be drawn off as a net hydrogen product gas stream. The reaction zone preferably comprises at least one radial flow reactor in which the catalyst gradually moves downward by gravity flow to allow the continuous replacement of used catalyst with catalyst having a higher activity. It is preferred that the reactants make at least two passes through a catalyst bed within the reaction zone. A detailed description of moving bed reactors of this type may be obtained by reference to U.S. Pat. Nos. 3,647,680; 3,706,536; 3,825,116; 3,839,196; 3,839,197; 3,854,887, 3,856,662 and 3,978,150.

The liquid stream withdrawn from the vapor-liquid separator is the effluent stream of the dehydrogenation reaction zone. This stream is passed into a fractionation system which preferably contains a single fractionation column referred to herein as a light ends stripping column. For MTBE production this column is designed and operated to eliminate all ethane and lighter boiling components from the net dehydrogenation zone effluent stream. It may also separate some and possibly all of the propylene into the light ends stream removed from this zone. The propylene may result from the dehydrogenation of propane present in the feed stream to the process or formed during the undesired cracking of butanes which produces the light ends removed from this zone.

The particular dehydrogenation conditions employed within the reaction zone may vary depending on such factors as the catalyst activity, feed carbon number and the desired conversion. The reaction zone conditions normally employed for butane dehydrogenation include a temperature of from about 500° to 700° C., a pressure of from 0.5 to about 10 atmospheres and a liquid hourly space velocity of about 1 to 20. The preferred operating temperature will be within the range of from about 550° to 660° C., and the preferred operating pressure is about 0.5 to 2 atmospheres. The preferred butane dehydrogenation catalyst is comprised of a platinum group component, preferably platinum, a tin component and an alkali metal component with a porous inorganic carrier material. Other catalytic compositions may be used within this zone if desired. The preferred catalyst contains an alkali metal component chosen from cesium, rubidium, potassium, sodium, and lithium. The preferred alkali metal is normally chosen from lithium and potassium, with potassium being preferred for isobutane. Preferred dehydrogenation catalysts comprise an alkali metal and a halogen such as potassium and chlorine in addition to the tin and platinum group components. The preparation and use of dehydrogenation catalysts is well known to those skilled in the art and further details as to suitable catalyst compositions is available in patents and other standard references.

To increase the supply of isobutane available to the process and also to convert the nonreactive normal paraffins of the recycle stream, the normal butane-rich deisobutanizer column sidecut stream is preferably passed into a butane isomerization unit. This unit comprises a reactor and auxiliary process equipment such as heaters, condensers, separatory vessels, etc. The isomerization unit preferably also contains a stripping column which eliminates light ends (hydrogen, methane, ethane) from the net effluent of the isomerization reactor. With the preferred catalyst, this stripping column will also remove volatile chloride compounds from the isomerization effluent. The core of the operation of this unit is passage of the sidecut stream through a reactor maintained at butane isomerization-promoting conditions including the presence of an acidic isomerization catalyst. This is normally a relatively low pressure operation performed at a pressure of from about 50 to 600 psig and at an elevated temperature as required by the activity of the catalyst. The average reactant temperature may be as high as 500° C., but is preferably between 100° and 320° C. It is normal practice to pass the butane through the reactor in admixture with between 1 and 10 moles of hydrogen per mole of butane to ensure vapor phase conditions and to suppress coke deposition on the catalyst. It is preferred that the butane is passed vertically through one or more fixed beds of catalyst located within the reactor at a liquid hourly space velocity between 1.0 and 6.0, but space velocities in the broad range of 0.5 to 12.0 can be employed if desired. The effluent of the isomerization reactor is normally separated into a hydrogen-rich recycle gas which is returned to the reactor and an isomerate-containing liquid stream which is passed into the stripping column. It is within the scope of the inventive concept that this liquid stream may be further fractionated within the isomerization unit to allow the recycling of normal butanes and the achievement of higher conversion rates, but this is not preferred. The bottoms stream of the stripping column is the net hydrocarbon effluent of the isomerization unit and is a mixture of isobutane and normal butane. This stream should contain 50 mole percent isobutane. Preferably this stream comprises 55 or 60 mole percent isobutane. Further details on the optional butane isomerization step of the subject process may be obtained by referring to the previously cited references.

The preferred isomerization-promoting catalyst for use in the isomerization unit comprises a platinum group component and a halogen component supported by an inorganic oxide carrier. The preferred platinum group components are platinum and palladium or a mixture of platinum and palladium, with platinum being especially preferred. A particularly preferred method for the production of an isomerization catalyst is presented in U.S. Pat. No. 2,999,074. The carrier material and the platinum group component are composited and the resulting material is mildly calcined. This calcination is normally carried out under carefully controlled conditions to remove physically adsorbed solvents such as water but to retain some chemically combined hydroxyl groups on the surface of the catalyst. Temperatures ranging from 350° to about 700° C. are usually satisfactory. The calcined composite is then reacted with a metal halide of the Friedel-Crafts type. Suitable metal halides include aluminum chloride, aluminum bromide, ferric chloride and zinc chloride, etc. Of these, aluminum chloride is particularly preferred.

I claim as my invention:

1. A process for the production of an ether which comprises the steps of:
   (a) passing a first process stream comprising an isoparaffin through a catalytic dehydrogenation reaction zone and thereby producing a reaction zone effluent stream comprising the isoparaffin and a corresponding isoolefin;
   (b) passing the reaction zone effluent stream and a hereinafter characterized second process stream into a stripping column and producing a stripping column bottoms stream comprising the isoparaffin, oxygen-containing hydrocarbonaceous compounds and the corresponding isoolefin;
   (c) passing the stripping column bottoms stream and a feed stream comprising an alcohol into an etherification zone maintained at etherification conditions, and withdrawing from the etherification zone a product stream comprising the ether and a hydrocarbon recycle stream comprising the isoparaffin and oxygen-containing hydrocarbonaceous compounds;
   (d) removing oxygen-containing hydrocarbonaceous compounds from the hydrocarbon recycle stream by contacting the hydrocarbon recycle stream with a selective sorbent at sorption-promoting conditions in a sorption zone to produce an isoparaffin-rich recycle stream;

(e) processing a first portion of said isoparaffin-rich recycle stream to produce additional amounts of the isoolefin;

(f) heating a second portion of said isoparaffin-rich recycle stream to a temperature of above 250° F.; and (g) regenerating sorbent in the sorption zone by a regeneration procedure which comprises contacting sorbent present in the sorption zone with a regeneration stream comprising said heated isoparaffin-rich recycle stream of step (f) at regeneration-promoting conditions to produce said previously referred to second process stream, which comprises the isoparaffin and oxygen-containing hydrocarbonaceous compounds.

2. The process of claim 1 further characterized in that the isoparaffin is isobutane.

3. The process of claim 2 further characterized in that the alcohol is ethanol.

4. The process of claim 2 further characterized in that the alcohol is methanol an the ether is methyl tertiary butyl ether.

5. The process of claim 4 further characterized in that the hydrocarbon recycle stream is rich in isobutane and comprises methanol and methyl tertiary butyl ether when withdrawn from the etherification zone.

* * * * *